(12) United States Patent
Uhlig et al.

(10) Patent No.: US 10,082,485 B2
(45) Date of Patent: Sep. 25, 2018

(54) METHOD AND APPARATUS FOR LEAKAGE FLUX TESTING

(71) Applicant: Institut Dr. Foerster GmbH & Co. KG, Reutlingen (DE)

(72) Inventors: Robert P. Uhlig, Bad Urach (DE); Friedrich Hecker, Reutlingen (DE)

(73) Assignee: Institut Dr. Foerster GmbH & Co. KG, Reutlingen (DE)

( * ) Notice: Subject to any disclaimer, the term of this patent is extended or adjusted under 35 U.S.C. 154(b) by 0 days.

(21) Appl. No.: 15/321,793

(22) PCT Filed: May 4, 2015

(86) PCT No.: PCT/EP2015/059657
§ 371 (c)(1),
(2) Date: Dec. 23, 2016

(87) PCT Pub. No.: WO2015/197239
PCT Pub. Date: Dec. 30, 2015

(65) Prior Publication Data
US 2017/0160236 A1    Jun. 8, 2017

(30) Foreign Application Priority Data

Jun. 27, 2014 (DE) .................. 10 2014 212 499

(51) Int. Cl.
*G01N 27/87* (2006.01)
(52) U.S. Cl.
CPC .................................. *G01N 27/87* (2013.01)
(58) Field of Classification Search
CPC ........ G01R 31/302; G01R 1/07; G01R 31/04; G01R 35/00; G01N 3/60; G01N 27/66;
(Continued)

(56) References Cited
U.S. PATENT DOCUMENTS

| 4,538,108 A | 8/1985 | Hueschelrath et al. |
| 4,814,705 A | 3/1989 | Saunderson |

(Continued)

FOREIGN PATENT DOCUMENTS

| EP | 0 073 017 A1 | 3/1983 |
| EP | 2 594 929 A2 | 5/2013 |
| WO | WO 93/16380 A1 | 8/1993 |

OTHER PUBLICATIONS

International Search Report (PCT/ISA/210) issued in PCT Application No. PCT/EP2015/059657 dated Aug. 4, 2015 with English translation (Six (6) pages).
(Continued)

*Primary Examiner* — Son Le
(74) *Attorney, Agent, or Firm* — Crowell & Moring LLP

(57) ABSTRACT

In a method for leakage flux testing of ferromagnetic material to be tested, in particular ferromagnetic pipes, for detecting defects, a testing volume of the material to be tested is magnetized by a constant magnetic field. A surface of the material to be tested is scanned by a probe arrangement for capturing magnetic leakage fields caused by defects. The probe arrangement has a probe array with a multiplicity of magnetic-field-sensitive probes arranged next to one another in a first direction and held at a finite testing distance from the surface of the material to be tested during the testing. Electrical probe signals are evaluated for qualifying the defects. Use is made of a probe arrangement in which the probes each have a probe width in the first direction which lies in the range from 20% of the testing distance up to 10 mm. An evaluation of the probe signals includes a mapping operation, in which signal information representing the probe signal is linked to spatial information representing the creation location of a probe signal for each probe signal in order to form spatially dependent signal data, a matrix-forming operation, in which the spatially dependent signal data, or signal data derived therefrom, are stored in fields, assigned with the correct location, of a basis matrix, and at least one evaluating operation, in which spatially dependent signal data from at least two fields of the basis matrix, directly or indirectly adjacent to one another in an evaluating direction, are linked to one another using at least one evaluating algorithm.

18 Claims, 9 Drawing Sheets

(58) Field of Classification Search
CPC ........ G01N 27/80; G01N 27/82; G01N 27/90; G01N 27/02; G01N 27/9006; G01N 27/025; G01N 27/72; G01N 27/9033; G01N 29/2412; G01N 2011/0086; G01N 27/87; G01B 7/06

See application file for complete search history.

(56) References Cited

U.S. PATENT DOCUMENTS

| | | | |
|---|---|---|---|
| 5,130,652 A * | 7/1992 | Kawakami | G01N 27/902 324/238 |
| 5,943,632 A | 8/1999 | Edens et al. | |
| 6,549,005 B1 | 4/2003 | Hay et al. | |
| 6,633,159 B1 | 10/2003 | Robar et al. | |
| 2002/0097045 A1* | 7/2002 | Crouzen | G01N 27/902 324/240 |
| 2004/0100256 A1 | 5/2004 | Fickert et al. | |
| 2009/0051358 A1* | 2/2009 | Shirasaka | G01N 27/902 324/238 |
| 2011/0037461 A1* | 2/2011 | Braun | G01N 27/87 324/240 |
| 2012/0109565 A1 | 5/2012 | Tsukada | |
| 2013/0119979 A1 | 5/2013 | Kaack et al. | |

OTHER PUBLICATIONS

German-language Written Opinion (PCT/ISA/237) issued in PCT Application No. PCT/EP2015/059657 dated Aug. 4, 2015 (Six (6) pages).

\* cited by examiner (SdT)

METHOD AND APPARATUS FOR LEAKAGE FLUX TESTING

FIELD OF THE INVENTION

The invention relates to a method for leakage flux testing of ferromagnetic material to be tested for detecting defects and to an apparatus, suitable for carrying out the method.

BACKGROUND OF THE INVENTION

Magnetic leakage flux methods are an important component of quality control, both in the production process and during the cyclically recurring testing of the finished parts, in nondestructive testing in respect of defects of semi-finished product and finished parts. In relation to some bothersome properties of the materials, such as roughness of the surface or scale coating in the case of hot-rolled products, magnetic leakage flux methods are less sensitive than e.g. the eddy current method or ultrasonic testing. As a result, there is a better ratio between used signal and noise signal (S/N ratio), as a result of which a more reliable fault detection is facilitated.

In an apparatus for detecting defects by means of leakage flux measurement, a test volume of the object to be tested is magnetized by means of a magnetizing device and scanned with the aid of at least one magnetic-field-sensitive probe (leakage flux probe) for detecting magnetic leakage fields caused by the defects. In the process, there is a relative movement in one scanning direction between the probe and the surface of the material to be tested. During the scanning, the probe is kept at a relatively small, but finite testing distance from the surface of the material to be tested. An individual probe passes over a testing track, the width of which is determined by the effective width of the probe transversely to the scanning direction.

The magnetic flux or magnetic field generated in the material to be tested by the magnetizing device is distributed substantially homogenously in space in material that is free from faults. In this case, there are also no substantial magnetic field gradients in the regions near the surface. Cracks and other defects, such as e.g. shrink holes, inclusions, or other inhomogeneities such as e.g. welding seams, etc., act as regions of increased magnetic resistance, and so field components in the vicinity of a defect are guided around the defect and pushed out of the metal into the region near the surface. The field components pushed thereout are detected in the leakage flux method for detecting the defects. In the case of a leakage flux measurement, a defect is detectable if the field components pushed out of the test object extend out to the region of the probe and cause a change in the field there which is sufficient for detection.

Depending on how the material to be tested is magnetized, the leakage flux testing methods or testing apparatuses are subdivided into methods or apparatuses with DC field magnetization (DC leakage flux testing) and methods or apparatuses with AC field magnetization (AC leakage flux testing).

When pipes are tested, capturing of both outer faults, i.e. faults or defects on the outer side of the pipe, and inner faults, i.e. faults on the pipe inner side and faults in the pipe wall, is sought after. To this end, use is usually made of methods with DC field magnetization (DC leakage flux testing). Here, a substantial advantage of DC field magnetization is used, specifically the great penetration depth, and so it is also possible to capture inner faults and faults in the pipe wall.

In the methods and apparatuses considered here, use is made of a probe arrangement for carrying out the testing, said probe arrangement having a probe array with a multiplicity of magnetic-field-sensitive probes, which are arranged next to one another in a first direction (width direction). The electrical probe signals, i.e. the electrical signals from the probes, or signals derived therefrom, are evaluated together by means of an evaluating device for qualifying the defects. By using a probe array, the testing width covered during a scanning process may be substantially larger than the testing width covered by an individual probe. Furthermore, the spatial resolution of the width direction is determined by the probe width of the individual probes. By using probe arrays, efficient testing of test objects in a continuous method is rendered possible.

When dimensioning the individual probes in respect of the probe width thereof, there usually is orientation on the basis of the so-called minimum fault length. The minimum fault length is the fault length (or defect length) above which the maximum amplitude of the probe signal, i.e. the highest testing sensitivity, and the maximum reproducibility are achieved. In the relevant standards, probe widths of 30 mm, or of one, or half a, minimum fault length, are specified, wherein the minimum fault length may be e.g. 25 mm or 50 mm, depending on standard. As a result of the reference to the minimum fault length, it is possible to obtain a good compromise between a number of probes which is as small as possible with, at the same time, a probe array which is as long or wide as possible (cost optimization) and the maximum admissible probe width (generally half the minimum fault length) considered to be required for a good reproducibility of the defect detection.

There is therefore needed a method and an apparatus for leakage flux testing, by means of probe arrays, of ferromagnetic material to be tested, which facilitate reliable testing in respect of faults of different types of fault.

SUMMARY OF THE INVENTION

In order to meet this need, the invention provides a method, and an apparatus for carrying out the method, for leakage flux testing of ferromagnetic material to be tested, in particular ferromagnetic pipes, for detecting defects. A test volume of the material to be tested is magnetized by a constant magnetic field. A surface of the material to be tested is scanned by a probe arrangement for capturing magnetic leakage fields caused by defects, said probe arrangement comprising a probe array with a multiplicity of magnetic-field-sensitive probes arranged next to one another in a first direction and held at a finite testing distance from the surface of the material to be tested during the testing. Electrical probe signals are evaluated for qualifying the defects. Use is made of a probe arrangement in which the probes each have a probe width in the first direction which lies in the range from 20% of the testing distance up to 10 mm, and in that an evaluation of the probe signals comprises the following steps: a mapping operation, in which signal information representing the probe signal is linked to spatial information representing the creation location of a probe signal for each probe signal in order to form spatially dependent signal data; a matrix-forming operation, in which the spatially dependent signal data, or signal data derived therefrom, are stored in fields, assigned with the correct location, of a basis matrix; and at least one evaluating operation, in which spatially dependent signal data from at least two fields of the basis matrix, adjacent to one another in an evaluating direction, are linked to one another using at least one evaluating algorithm.

In the methods and apparatuses in accordance with the claimed invention, the probe width of the individual probes of a probe array is substantially reduced in relation to conventional approaches. The probe width is no longer oriented on the minimum fault length but on the smallest leakage flux width to be expected; the latter is substantially determined by the distance between the probe and the material surface (testing distance). A probe array with a local high resolution in the width direction is provided. Approximately one fifth of the testing distance is considered to be a technically expedient lower limit for the probe width. In the case of currently typical testing distances in the range of a few tenths of a millimeter up to approximately 2 mm, a lower limit of the probe width of 0.1 mm is currently considered expedient, and so—in accordance with alternative phrasing—the probe width should lie in the range from 0.1 mm to 10 mm. In the case of probe widths of individual probes of more than 10 mm, the sought-after high spatial resolution of the individual probes may, in general, no longer be fully achieved. Currently, probe widths in the range from 0.5 mm to 3 mm appear particularly advantageous.

The evaluation of the probe signals comprises a plurality of operations which are matched to one another and which, in particular, are matched to the probe arrangement with a high resolution in terms of location or space.

In a mapping operation, signal information representing the probe signal is linked to spatial information representing the creation location of the probe signal in a scanned surface region for each probe signal. As a result, spatially dependent signal data are formed. The mapping operation creates a unique assignment between signal information and location information and may serve as a basis for generating a "map" of the respectively scanned surface region. By way of example, signals of rotary encoders (angular position encoders) and/or linear encoders of the testing apparatus may be used to ascertain the location information.

In a matrix-forming operation, the spatially dependent signal data (or signal data derived therefrom) are stored in fields or elements, assigned with the correct location, of a basis matrix. Here, deviating from a conventional definition of a matrix from mathematics (two-dimensional rectangular arrangement of elements in rows and columns), the term "matrix" denotes an n-dimensional array of elements, where n is greater than or equal to two. Hence, a matrix within the meaning of the application may have more than two dimensions, for example three or four. In the broadest sense, the matrix provides an assignment between location information, signal information and, possibly, further information to parameters which influence the method and the results thereof.

A first dimension of the basis matrix represents signal information, which contains information about the leakage flux measured at a specific location of the surface of the material to be tested. This signal information may be specified as a scalar variable or as a vector variable. By way of example, the signal amplitude or a selected component of the leakage flux may be considered as scalar variable, which component may represent, for example, the normal component or a tangential component of the measured leakage flux. The signal information may also represent the complete vector of the leakage flux (Bx-, By- and Bz-component).

A second dimension of the basis matrix represents a position in the first direction, i.e. in the width direction of the probe array (transversely to the scanning direction). If a dedicated channel is assigned to each probe of the probe array, the position in the first direction may also be specified by the channel number.

A third dimension of the basis matrix represents a position in the scanning direction. This direction may be perpendicular to the first direction or be aligned at a more or less acute angle in relation thereto.

Further dimensions are also possible. By way of example, forming a multidimensional arrangement of elements or fields, in which the magnetic flux density is stored as a vector depending on probe, location in the passage direction and lift off (testing distance), would be conceivable. Then, the matrix forms a special form of a tensor for arrays, in which the probes are arranged as described.

The basis matrix or the field information contained in the individual elements or fields serves as a basis, for the further operations of the evaluation. Here, at least one evaluating operation is carried out, in which spatially dependent signal data from at least two fields of the basis matrix, directly or indirectly adjacent to one another in a (virtual) evaluating direction, are linked to one another using at least one evaluating algorithm.

Therefore, this evaluation works with the "map" of the surface region represented in the basis matrix in order to evaluate the information contained in the basis matrix, or in the fields or elements thereof, according to one or more criteria. Here, the probe information from one of the individual probes of the probe array is evaluated together with the probe information from at least one further probe, adjacent in the evaluating direction, of the probe array, and/or an adjacent testing track. Here, it is possible to take into account that the conditions between two locations situated closely adjacent to one another on the material to be tested, which are scanned by probes which are situated closely adjacent to one another, generally do not have a discontinuous jump, and so a mutual dependence of the probe signals may be taken into account.

This evaluation may be carried out within probes of the same probe array. If a plurality of probe arrays are provided, the probes of which scan the same or mutually adjacent testing tracks, the evaluation may also operate in a probe-array-overarching manner such that the signals from probes of different probe arrays are evaluated together with an assignment with the correct location.

The probe width of the individual probes is substantially smaller than half a minimum fault length, i.e. significantly smaller than what was previously conventional. As a result, testing with a high spatial resolution is rendered possible, at least in the first direction. Nevertheless, standard defects, which are represented by the minimum fault length, may be found at least as well as previously since a wider effective probe width adapted to the minimum fault length may also be created or simulated where necessary as a result of the common evaluation of the probe signals of adjacent probes and/or testing tracks. However, moreover, it is also possible to reliably find and identify further defects, for which conventional testing methods and apparatuses were "blind" or "visually deficient" (i.e. less sensitive).

Preferably, bipolar signal information is used when forming the basis matrix, i.e. "raw" signal information from non-rectified probe signals. As a result, the evaluation may also make use of information which would be lost by rectification.

All probes of a probe array may be arranged next to one another in a single straight row in the first direction (width direction). The effective widths of adjacent probes may overlap on account of the finite testing distance. It is also possible to subdivide the probes into two (or more) mutually parallel rows and arrange these offset to one another in the width directions in such a way that the probes sit "in gaps". As a result, a coverage without gaps of the entire width to be tested is possible in the width direction.

In particular, Hall probes or MR probes (probes which use a magnetoresistive effect for magnetic field detection, e.g. GMR (giant magnetoresistance), AMR (anisotropic magnetoresistance), CMR (colossal magnetoresistance) or TMR (tunnel magnetoresistance)) or inductive probes (in particular coils) or any other type of magnetic-field-sensitive probes may be considered as probes.

In order, where possible, only to process those signals in the subsequent signal processing which may in fact have relevance for the testing situation, provision is made in some variants of the method for pre-filtering of the probe signals in the apparatus, carried out before the mapping operation, by means of a band-pass filter with adjustable limit frequencies. Here, a lower limit frequency is set to a lowest frequency of the probe signals to be expected and an upper limit frequency is set to a highest frequency of the probe signals to be expected. As a result, coarse pre-filtering is possible. The limit frequencies may be adjusted depending on the pass-over speed of the probe, the testing distance, the smallest and largest fault width and fault depth to be detected, optionally on the wall thickness (in the case of pipes), and possibly on other boundary conditions. As a result, the testing may be matched to specific testing conditions, some sources of disturbance are removed from the signals and the relevance of the further processed signals is increased. By way of example, low-frequency signal components which carry no information relevant to the material to be tested during the testing situation may be removed by suitable pre-selection of a lower limit frequency. By way of example, the highest limit frequency may be set in such a way that frequencies which are higher than those frequencies which typically originate from small cracks on the surface of the material to be tested are filtered out. From experience, it is said frequencies of small cracks which provide the highest relevant frequency components.

In some embodiments, the evaluation of the signals may be optimized specifically for different fault types. In some embodiments, provision is made for filtering by means of one or more band-pass filters with adjustable limit frequencies carried out after the mapping operation, said filtering depending on the fault type, wherein a lower limit frequency of a band-pass filter is set to a lowest frequency of the probe signals and an upper limit frequency of the band-pass filter is set to a highest frequency of the probe signals, respectively to be expected for a predetermined fault type. Hence, fault-type-dependent band-pass filtering is undertaken. Each one of these filtering processes opens up a specific fault type path, wherein the subsequent evaluation steps within a fault type path are specific to the respective fault type. Fault type data, which make available a fault catalog in respect of the fault types, may be stored in a memory of the apparatus. By way of example, a fault-type catalog may contain the following fault types: outer fault, inner fault (e.g. in the case of pipes), bores with different diameters, peel faults, oblique faults with different orientations across the first direction and the second direction, bottom splashes, shrink holes, casting powder inclusions, etc.

In some embodiments, a particularly high user-friendliness and high specificity in the detection of faults is given by virtue of the number of band-passes for the fault-type-dependent filtering being configurable such that the apparatus or the method may be ideally matched to a specific testing situation. Preferably, three, four, five, six or more band-pass filters with different limit frequencies are used for the filtering which is dependent on the fault type. Compared to conventional methods and apparatuses, the capability of distinction is significantly increased thereby, said conventional methods and apparatuses substantially only having been able to distinguish between inner faults (resulting in lower frequencies) and outer faults (resulting in higher frequencies) during pipe testing.

Opening up different fault path types for the evaluation may also take place in other phases of the evaluating process, in particular on the basis of spatially dependent signal data which are stored in the fields of the basis matrix.

As mentioned previously, the basis matrix or the field information contained in the individual fields of the basis matrix serves as a basis for further operations of the evaluation.

Preferably, one or more evaluation operations which are designed as filtering operations of spatially dependent signal data over a predetermined number of mutually adjacent fields in a predetermined evaluating direction are carried out. Here, in particular, the term "filtering operation" should comprise those operations with which specific constituents or features may be removed from a signal, for example specific frequency components or noise. Here, it is possible, in principle, to carry out evaluating operations in evaluating directions, in principle any evaluating directions, of the basis matrix with any filters which, however, are particularly suitable for the fault detection in respect of their (one or more) limit frequencies. The filtering operations include, in particular, operations with a low-pass characteristic (low-pass filtering), operations with a high-pass characteristic (high-pass filtering) and operations with a band-pass characteristic (band-pass filtering), wherein, in principle, the band-pass filtering may be considered to be a combination of high-pass filtering and low-pass filtering with specific limit frequencies.

In some embodiments, provision is made for an evaluation operation to comprise a smoothing operation of spatially dependent signal data over a predetermined number of mutually adjacent fields in an evaluating direction (smoothing direction). Here, smoothing to each of its neighbors is possible for each field content. By way of example, there are eight direct neighbors for each field not lying on the edge in the case of a two-dimensional basis matrix. In principle, any algorithm with a low-pass characteristic for reducing the dynamics comes into question for the smoothing operation. By way of example, the smoothing operation may be forming a (weighted or unweighted) moving average or low-pass filtering. Forming a (weighted or unweighted) sum may also be used as a smoothing operation.

The evaluating direction of the smoothing operation may correspond to the first direction, i.e. the direction in which the probes of a probe array lie next to one another. In this way, the signal information of two or more probes lying next to one another may be smoothed (optionally also in a probe-array-overarching manner). Smoothing may be carried out over a plurality of channel numbers. If statistical noise is present, such smoothing may improve the signal-to-noise ratio. The number of signals or probes or testing tracks over which a smoothing operation is intended to be carried out may be predetermined. The selected number of probes or testing tracks over which integration is carried out determines the "effective probe width" which may be generated thereby. By way of example, the number may be from two to ten, but may possibly also be more than 10, for example in the range between 10 and 30. As a result of this, it is possible to adapt the testing characteristic to a minimum fault length.

Alternatively, or additionally, it is also possible for the evaluating direction of an evaluating operation to correspond to the second direction, which extends perpendicular to the first direction in which the probes lie next to one another. The second direction may, either exactly or approximately, correspond to the scanning direction and corresponds to the time axis of the test. In particular, the evaluating operations which may be carried out in the second direction include the aforementioned filtering operations, which also include the smoothing operation.

In particular, it is also possible to carry out fault-type-dependent band-pass filtering in the second direction. Optionally, this may replace the aforementioned fault-type-dependent filtering occurring outside of the basis matrix. One or more band-pass filters with adjustable limit frequencies, which are respectively matched to a specific fault type, may also be realized within the scope of this band-pass filtering in the second direction.

It is known that the level of leakage flux signals of a fault reduces the more the fault deviates from the (in view of the testing ideal) orthogonal position in relation to the main magnetization direction. As a result, oblique faults may not be identified during the testing or may be assessed incorrectly in respect of the size and relevance thereof. Method and apparatus in accordance with the claimed invention are able to supply meaningful test results, even in the case of oblique faults. To this end, provision is made in some embodiments for the evaluating direction in at least one evaluating operation to correspond to an oblique direction which extends transversely in relation to the first direction and transversely in relation to the second direction. Evaluations in different oblique directions representing different angular positions for an oblique fault are also possible.

In order to take account of the influence of the oblique position of the fault in relation to the main magnetization direction, provision is preferably made of an oblique fault compensating operation, in which an angle difference between an oblique fault direction and a field line direction of the magnetization field is determined and spatially dependent signal data of an oblique fault are corrected by a compensation factor dependent on the angle position. Here, there may be support from relationships determined empirically or analytically or in calibration procedures, which relationships, for example, may be stored in a lookup table of a memory in the apparatus.

Particular variants of the method in the apparatus are characterized by automatically ascertaining the angle position of oblique faults extending in an oblique direction which extends transversely in relation to the first direction and transversely in relation to the second direction. These methods may facilitate an optimized oblique fault detection without a priori knowledge about the oblique positions to be expected.

In one variant of automatically ascertaining the angle position of oblique errors, the fields of the basis matrix are evaluated automatically over a plurality of oblique directions in different evaluating directions within a predeterminable angle range and the oblique direction in which a maximum mean signal amplitude (taking into account the angular dependence) occurs is ascertained, taking into account the known angular dependence, which e.g. is stored in a table, of the signal amplitude on oblique faults. This oblique direction then corresponds to the alignment or angle position of the oblique fault. That is to say, when automatically ascertaining the angle position, certain predeterminable angle ranges may be scanned automatically at predeterminable increments in order to ascertain the oblique direction in which an oblique fault is aligned.

By way of example, elongate, metallic material to be tested may have disturbance zones caused by production or caused by processes, said disturbance zones usually extending in the longitudinal direction of the material to be tested or under a small angle to the longitudinal direction. By way of example, seams of welded pipes or wall thickness deviations caused by stretch-reducing mills, so-called inner polygons, may impair testing by virtue of these disturbance zones generating signal components which impair the defect testing. In embodiments of the method and the apparatus, such problems may be suppressed by virtue of at least one evaluating operation being a difference-forming operation, in which a difference between spatially dependent signal data of two fields of the basis matrix lying in a difference-forming direction and at a difference distance from one another is ascertained. This option for eliminating interference from signals is yet to be explained in more detail below on the basis of exemplary embodiments.

Here, it is possible, for example, for the difference-forming direction to correspond to the first direction. As a result of this, it is possible, for example, to mask the signals arising from longitudinal seams in pipes in the case of rotating test systems. It is also possible for the difference-forming direction to extend obliquely to the first direction. As a result of this, it is possible to mask signals which, for example, are caused by longitudinal seams with a certain amount of twist. It is possible to carry out a plurality of difference-forming operations in different difference-forming directions and/or over different difference distances in order to remove the signal components of disturbances with different causes and hence improve the desired defect characterization. It is also possible for the direction of one or more disturbance sources to be identified automatically and for the difference-forming operation to be applied to these directions.

In one variant, the difference distance is matched to the minimum fault length predetermined for the respective process, wherein the difference distance lies between the minimum fault length and five times the minimum fault length. As a result of this, it is possible to obtain a compromise between an optimum disturbance signal suppression (this demands a difference distance that is as large as possible as a matter of principle) and obtaining the fault information (this demands a difference distance of the order of the minimum fault length as a matter of principle and is dependent on fault type).

Suitable devices are provided at the apparatus for leakage flux testing in order to carry out the individual method steps. After digitizing the probe signals which are initially present in analog form, the individual method steps may be realized by suitable modules of evaluation software.

Indicating defects, marking defective positions, etc., may be realized in a manner similar to conventional testing methods and testing apparatuses.

BRIEF DESCRIPTION OF THE DRAWINGS

Further advantages and aspects of the invention emerge from the claims and the following description of preferred exemplary embodiments of the invention, which are explained below on the basis of the figures.

DETAILED DESCRIPTION OF THE PREFERRED EMBODIMENTS

Below, exemplary embodiments of the claimed invention are explained on the basis of an apparatus for leakage flux testing of ferromagnetic material to be tested, in the form of hot-rolled ferromagnetic pipes in a continuous method. The apparatus is configured for the detection of defects or inadequacies or imperfections of different types and may, for example, reliably detect rolling faults both on the pipe inner side (inner fault) and on the pipe outer side (outer fault). In so doing, it is possible to reliably find and characterize longitudinal faults (faults with the main direction of extent parallel to the pipe longitudinal axis) and transverse faults (faults with the main direction of extent in the circumferential direction or perpendicular to the pipe longitudinal axis) and oblique faults (transversely to the longitudinal direction and to the circumferential direction).

Figure 1A:
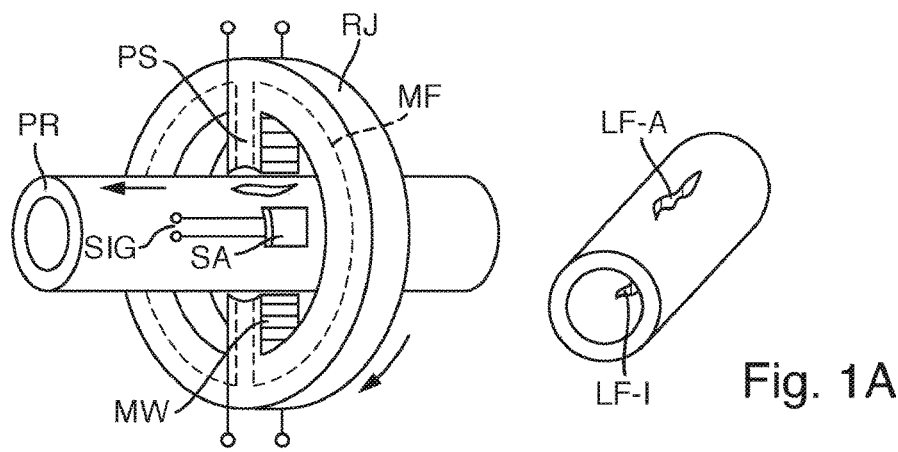
FIGS. 1A-1B show partial systems of an exemplary embodiment of an apparatus for leakage flux testing of ferromagnetic material to be tested, comprising a rotating partial system (FIG. 1A) and a stationary partial system (FIG. 1B)
Figure 1B:
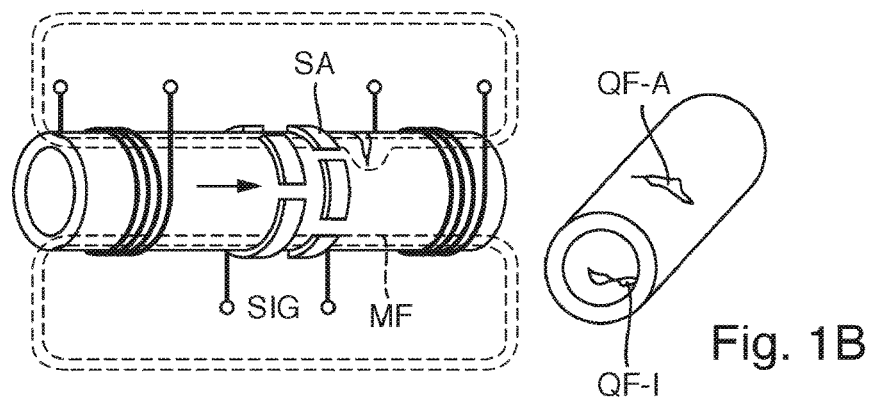

In one embodiment, two partial systems are integrated in a multi-testing block. A rotating partial system is provided for longitudinal fault testing, the fundamental principle of which is explained on the basis of FIG. 1A. A stationary partial system with a ring-shaped arrangement comprising a plurality of sensor arrays distributed around the circumference of the arrangement, for example in accordance with the arrangement in FIG. 1B, is provided for transverse fault testing. The partial systems are arranged in succession in the passage direction of the pipe, wherein the sequence may be arbitrary. In other embodiments not depicted in any more detail, a single system may suffice, for example a single rotating system.

Figure 2:
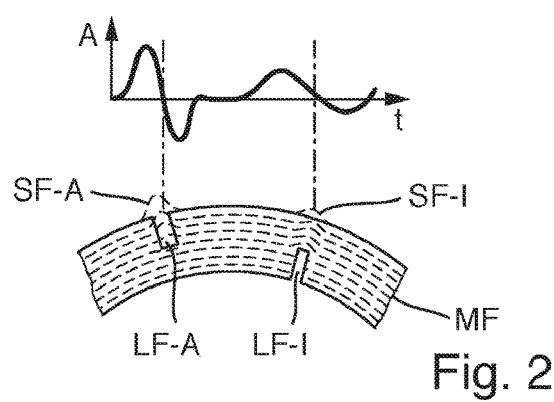
FIG. 2 shows fault—type-specific leakage flux fields at a section through a pipe.

The rotating partial system has a rotating head with a ring yoke RJ which rotates around the material PR to be tested and which has pole shoes PS aligned radially in relation to the test object surface at diametrically opposite points, with magnetization windings MW being attached to said pole shoes. As a result, a magnetic flux or magnetic field MF (DC field) is generated in the interior of the test object, the field lines of which extend in the circumferential direction of the test object, i.e. perpendicular to the longitudinal direction of the pipe. Testing heads are respectively arranged on the rotor in the circumferential direction between the pole shoes, said testing heads each containing one or more probe arrays SA, with each probe array comprising a multiplicity of individual probes. The ring yoke together with the pole shoes and the testing heads rotates with rotational speeds between approximately 60 and approximately 1200 min-1 during testing, depending on the type of probes. The pipe to be tested is simultaneously moved forward in the passage direction with a testing speed (e.g. up to 3 m/s or more). Here, the testing heads slide along the pipe surface and scan the latter without gaps along a helical path. The probes SO of the probe array are arranged within the testing heads at a small testing distance AB from the surface OB of the material to be tested, wherein said testing distance may be of the order, for example, of 0.2 mm to 1 mm (cf. FIG. 3). As a result of the magnetic field lines extending in the circumferential direction, this testing is particularly sensitive to longitudinal faults LF-A on the outer side of the pipe and longitudinal faults LF-I on the inner side of the pipe, which disturb the magnetic flux in the circumferential direction to maximum extent and, as a result thereof, generate strong leakage flux fields (FIG. 2).

In the case of the stationary system (FIG. 1B) for transverse fault testing, use is made of a DC field magnetization device (not depicted in any more detail) which generates a magnetic field MF in the longitudinal direction of the passing-through pipe. Two rings of probe arrays with probe arrays SA arranged in gaps in the circumferential direction are arranged around the test object in a ring-shaped manner and scan the test object in the longitudinal direction thereof during the continuous testing. Since the magnetic flux extends in the longitudinal direction, it is disturbed particularly strongly by transverse faults on the outer side (QF-A) and transverse faults on the inner side (QF-I), said faults extending in the circumferential direction, such that this arrangement has high testing sensitivity for transverse fault testing.

The electric signals SIG of the probes of the probe arrays, i.e. the probe signals, are fed to a common evaluating device in which the qualification of the defects is carried out.

Each type of faults causes certain, fault-type-specific leakage flux fields, the properties of which may be identified from the signal form and the frequencies contained in the signal. By way of example, FIG. 2 shows a section through a pipe perpendicular to the longitudinal direction and the magnetic field lines of the magnetization field MF extending in the circumferential direction. An outer fault LF-A extending in the longitudinal direction generates a leakage flux field SF-A which is relatively tightly concentrated in the vicinity of the outer fault. By contrast, an inner fault LF-I with the same dimensions extending in the longitudinal direction generates a locally strongly smeared or widened or broadened leakage flux field SF-I with a lower amplitude on the outer side of the pipe. Typical signal forms of the probe signals when a probe passes over in the circumferential direction are shown above the leakage flux fields in each case. Here, the y-axis corresponds to the signal amplitude A and the x-axis corresponds to the time t or the location during the circulation of the probe. It can immediately be identified that the outer fault causes a probe signal with higher frequency signal components than an inner fault. As a result, it is plausible to be able to detect, identify and, where necessary, distinguish different fault types by, inter alia, the frequency spectrum of the probe signals generated in each case.

Figure 3:
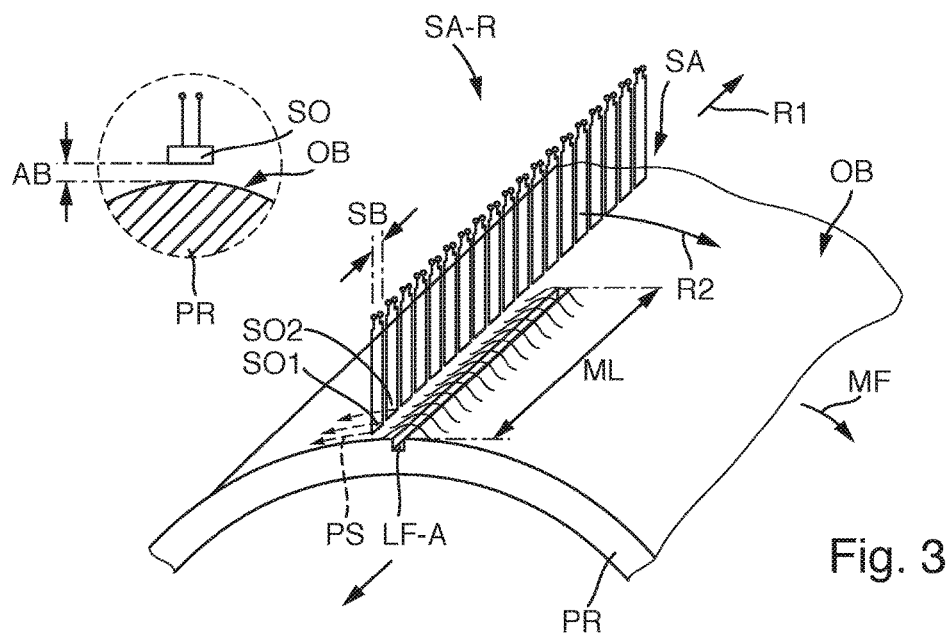
FIG. 3 shows details in respect of configuring the probe arrangement for a rotating partial system in accordance with one exemplary embodiment.
Figure 4:
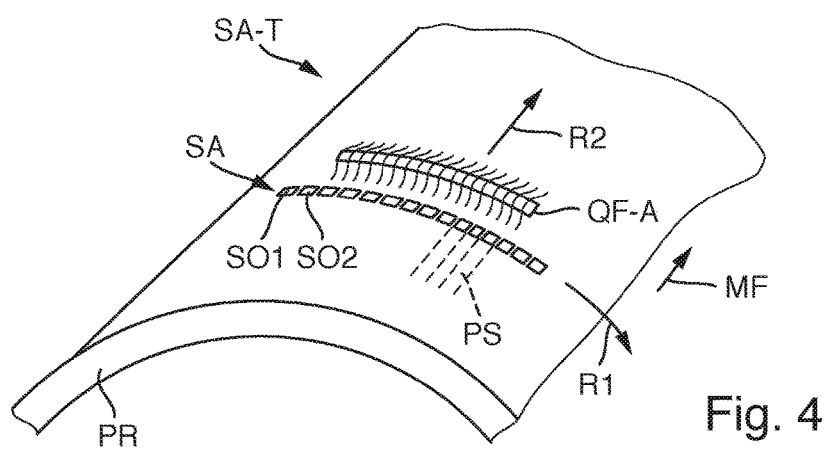
FIG. 4 shows details in respect of configuring the probe arrangement for a stationary partial system in accordance with one exemplary embodiment.

FIGS. 3 and 4 are now used to explain details for configuring the probe arrangements for the rotating system (FIG. 3) and the stationary system (FIG. 4). The probe arrangement SA-R for the rotating system has a multiplicity of nominally identical individual probes SO1, SO2 etc., which form a probe array SA and are arranged in a straight line along a first direction R1 extending parallel to the longitudinal axis of the pipe. The probe array SA is installed in a testing head. In the case of a rotating system, the probe arrangement moves as a whole around the test object in the circumferential direction of the test object, along a second direction R2 which extends perpendicular to the first direction R1. As a result of the longitudinal movement of the test object PR occurring at the same time, each one of the individual probes SO1, SO2 scans a relatively narrow testing track PS, which extends around the test object in a spiral form, with the testing track extending at an angle to the first direction and to the second direction. Together, all probes of the probe array scan a relatively high testing width with a multiplicity of testing tracks which are parallel to one another.

The shown outer longitudinal fault LF-A is a standard defect with a minimum fault length ML defined for this test, said minimum fault length being 25 mm in the exemplary case. The probe widths SB of the individual probes SO1, SO2 etc. are only a fraction of the minimum fault length in the first direction. In the exemplary case, the probe width measured in the first direction R1 lies in the range between 0.5 mm and 3 mm, which in this case corresponds to the range between 50% of the testing distance and approximately two to three times the testing distance.

A corresponding arrangement emerges in the probe arrangement SA-T for transverse fault testing (cf. FIG. 4). The probe arrangement SA-T has a multiplicity of individual probes SO1, SO2, etc., which are arranged next to one another in a row in the first direction R1, the first direction in this case corresponding to the circumferential direction of the material PR to be tested. The probe arrangement is stationary while the material to be tested moves parallel to the longitudinal direction thereof such that the probe array scans the test object surface in a scanning direction corresponding to the second direction R2 which is perpendicular to the first direction R1. Here too, each individual probe covers a relatively narrow testing track PS, with the totality of the testing tracks in the circumferential direction resulting in a many times larger testing width of the probe arrangement. The magnetic field MF extending in the longitudinal direction of the pipe is pushed out of the test object material at a transverse fault QF-A and detected by means of the probes of the probe array SA. Here too, the probe width SB of the individual probes, as measured in the first direction R1, is only approximately 0.5 mm to 3 mm, while the outer transverse fault QF-A has the minimum fault length of 25 mm provided for the test.

Figure 5:
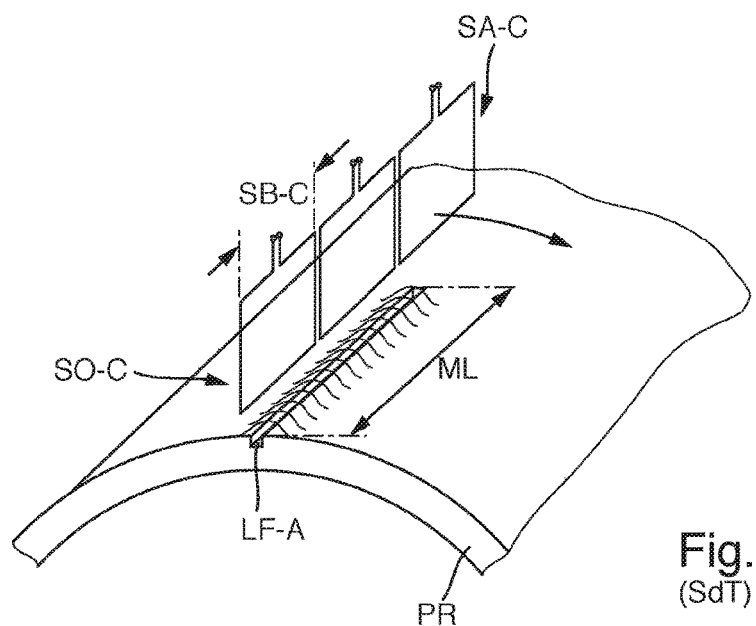
FIG. 5 shows details in respect of configuring the probe arrangement for a rotating partial system in accordance with the prior art (SdT)

The probe widths which are reduced in relation to the prior art (SdT) are elucidated on the basis of FIG. 5, in which a conventional probe array SA-C with three individual probes SO-C for a conventional rotating testing system is shown in the same testing situation as in FIG. 3. The individual probes are dimensioned in conventional fashion, and so the probe width SB-C thereof in the first direction (longitudinal direction of the pipe) corresponds to approximately 50% of the minimum fault length ML, i.e. the test fault length of the outer longitudinal fault LF-A (25 mm).

While the extent of the probe width in conventional systems is guided by this minimum fault length, the probe width of the individual probes in exemplary embodiments of the invention is guided by the smallest leakage flux width to be expected, which, inter alia, is determined by the testing distance of the probe from the material surface. The novel probe arrangements are able to scan the test object surface with a substantially higher spatial resolution than conventional probe arrangements for comparable purposes. As a result of suitable signal processing or evaluation of the probe signals, faults with the minimum fault length may nevertheless be detected with at least comparable testing sensitivity, with, additionally, numerous further evaluation possibilities and numerous other detection options emerging.

Figure 6:
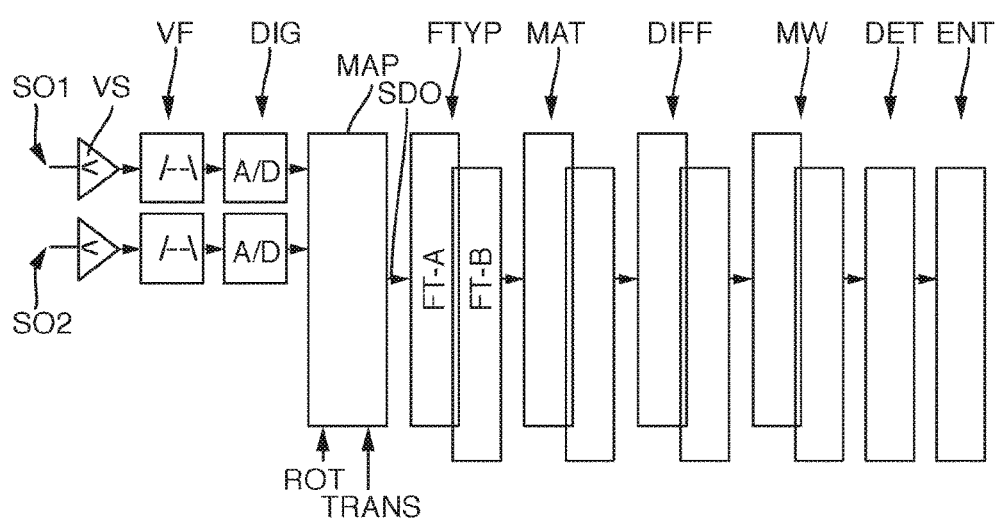
FIG. 6 shows an exemplary embodiment of an evaluating device.

In order to ease the understanding of the subsequent embodiment, FIG. 6 shows a block diagram of the evaluating device AW for the entire evaluation of probe signals in one embodiment, with the individual components representing individual steps of the signal evaluation and/or components of the evaluating device. Shown in an exemplary manner are paths for probe signals from two probes SO1, SO2, with a corresponding path being provided for each probe.

The probe signals from the first probe SO1 initially pass through gain matching VS before they are pre-filtered in a pre-filtering device VF. Here, the signal components of each individual probe are filtered by a band pass, the limit frequencies of which are set, or may be set, to the lowest and highest frequency of the leakage flux signals to be expected, depending on the probe passing speed, the testing distance from the material surface, the wall thickness and the smallest, and largest, fault width to be detected. By means of the coarse pre-filtering, it is possible to filter out signal components which are clearly irrelevant, and so the following evaluation is simplified.

The bipolar signals which were pre-filtered by the bandpass filtering are then converted into digital signal information, or digitized, by an analog-digital filter unit DIG.

A subsequent mapping unit MAP is configured to link the signal information linked to the probe signal to spatial information in relation to the creation location of the probe signal for each probe signal. To this end, the mapping unit processes, inter alia, signals from linear encoders TRANS and rotary encoders ROT. By way of example, the information about the rotational position of the rotating system is ascertained by means of a rotary encoder in order to identify the position of a probe when generating the associated signal at the circumference of the test object. Linear encoders serve to identify the corresponding position in the longitudinal direction of the test object. Then, spatially dependent signal data SDO are available at the output of the mapping unit, said signal data being processed further during the subsequent evaluation operations.

The magnetic-field-sensitive probes, which may be constructed with, for example, coils, Hall sensors or the like, preferably capture the normal component of the leakage flux. Alternatively, or additionally, it is also possible to capture the tangential component of the leakage flux or the complete vector of the leakage flux (Bx-, By- and Bz-component).

The mapping device MAP is followed by fault—type-dependent band passes FTYP for fault—type-dependent band-pass filtering. These facilitate filtering of each individual probe signal, or the corresponding spatially dependent signal data, in accordance with predeterminable limit frequencies which may be set in accordance with the signal frequency to be expected for the various fault types (for example longitudinal or transverse faults, outer/inner faults, bores with different diameters, natural faults such as peels, etc.). In the apparatus, the number of band passes is configurable, i.e., it may be matched in an ideal manner to the testing situation where necessary. Even though FIG. 6 only shows two band passes for fault type A (FT-A) and fault type B (FT-B), it is possible to provide substantially more than two fault—type-dependent band passes with corresponding filtering options in order to undertake specific filtering for a multiplicity of faults.

All subsequent evaluation operations may be undertaken separately for each fault type such that a fault—type-specific signal evaluation is obtained.

In the exemplary case, a matrix-forming unit MAT, in which a matrix-forming operation is carried out, follows in the signal flow of the evaluating device. In the matrix-forming operation, the spatially dependent signal data, or signal data derived therefrom, which were also filtered in a fault—type-dependent manner in the example in case, are stored in fields, assigned with the correct location, of a basis matrix. To this end, provision can be made of a specific storage region of a memory of the evaluating device.

In the exemplary case, a multidimensional basis matrix comprising the leakage flux values (or corresponding data) and the spatial coordinates thereof (or corresponding data) is generated from the pre-filtered leakage flux signals for each band pass, i.e. for each fault type. In the exemplary case, the information taken into account when forming the matrix may be divided into three dimensions (cf. FIGS. 8 to 12).

The first dimension contains the signal information in the form of an amplitude of the leakage flux signal. Here, the non-rectified bipolar signal information is taken into account. By way of example, it is possible to store only the normal component of the leakage flux or only the horizontal component of the leakage flux or else the complete leakage flux vector with Bx-, By- and Bz-components and keep it for the further evaluation.

The location information is encoded in the second dimension and in the third dimension. By way of example, the longitudinal position LP of the creation location of the leakage flux value on the material to be tested is stored in the second dimension. In the case of a rotating system, the resolution here lies in the region of a probe width of an individual probe. In the case of the stationary system, the resolution in relation to the longitudinal position corresponds to the scanning frequency which is matched to the maximum frequency of the band pass underlying the matrix.

The third dimension corresponds to the circumferential position UP of the creation location of the leakage flux value. Here, the resolution in the rotating system corresponds to the scanning frequency which is matched to the maximum frequency of the band pass underlying the matrix, while the resolution in the circumferential direction in the case of the stationary system corresponds to a probe width of an individual probe.

It is possible to carry out different evaluating operations using the spatially dependent signal data within the basis matrices. Some examples are explained below.

After the preceding band-pass filterings, the signals of the individual probes contain the sought-after use information within the frequency regions to be processed further, possibly superposed by disturbance information which, for example, is traced back to the surface roughness which is not critical to the function thereof. In order to improve the reliability of the evaluation results, it is possible, for example, to carry out a smoothing operation over a predetermined number of mutually adjacent fields of a basis matrix.

Figure 7A:
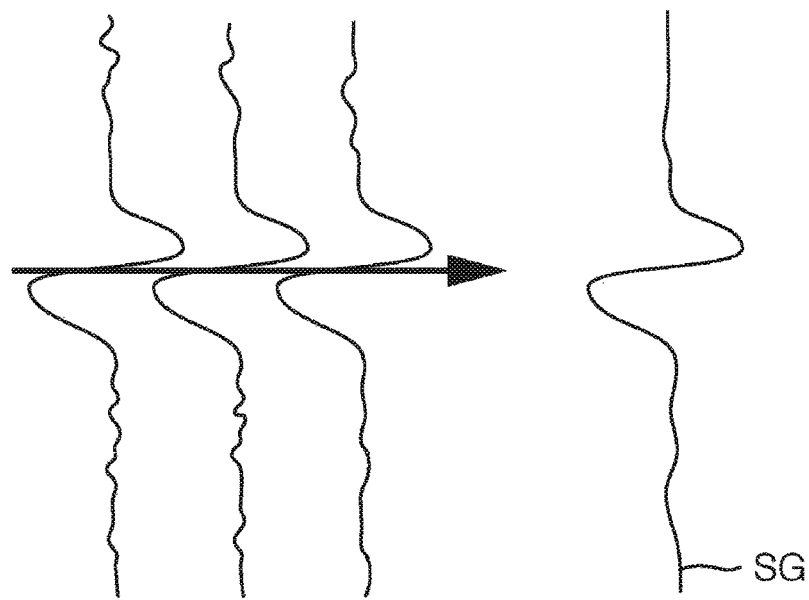
FIGS. 7A-7B show signals in the case of a smoothing operation by forming an average in the case of longitudinal fault testing (FIG. 7A) and transverse fault testing (FIG. 7B)
Figure 7B:
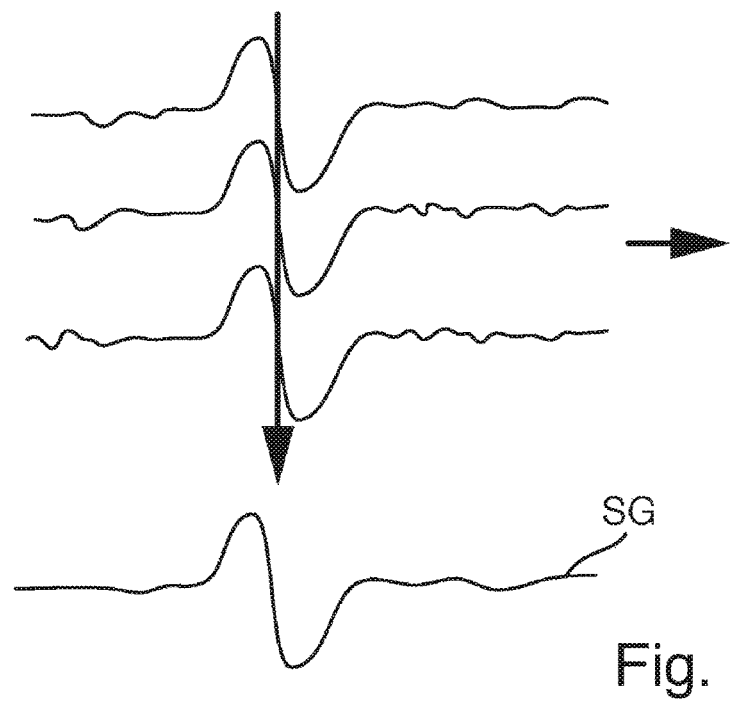

FIGS. 7 to 9 are used to explain how forming a moving average may improve the quality of the signals to be processed further. To this end, the evaluating device of FIG. 6 comprises an average forming unit MW. To this end, FIG. 7 shows, in FIG. 7A, the process of forming an average over three individual probe signals, which each indicate the normal component of the leakage flux during longitudinal fault testing. FIG. 7B shows the corresponding individual probe signals in the case of transverse fault testing. It is possible to identify that the signals SG smoothed by forming an average have a better signal-to-noise ratio than the initial signals.

Figures 8A, 8B:
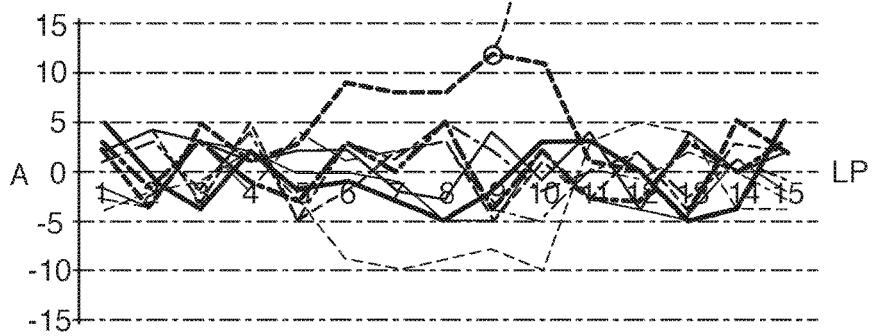
FIGS. 8A-8B show an example for a basis matrix in the case of a rotating system (FIG. 8A), wherein signal data from non-rectified probe signals are entered in the individual fields, and a diagram (FIG. 8B), in which the longitudinal position (channel number) is plotted along the x-axis and the signal amplitude A of the individual signals from the individual channels is plotted along the y-axis.

FIG. 8A shows an example of a basis matrix BM for a rotating system, in which signal data from non-rectified (bipolar) probe signals are entered into the individual fields. The signal data are symbolized by signed numbers. The second dimension of the basis matrix, specifically the longitudinal position LP of the creation location of the respective signal, is plotted in the horizontal direction. The third dimension, specifically the circumferential position UP, is plotted in the direction perpendicular thereto. In the example of a rotating testing system, the longitudinal position LP corresponds to the channel number of the individual probes of the probe array. The circumferential position UP correlates with the time axis of testing. FIG. 8B shows the channel number, i.e. the longitudinal position LP, along the x axis, while the signal amplitude A of the individual signals (curves) of the individual channels is plotted on the y-axis.

Figures 9A, 9B:
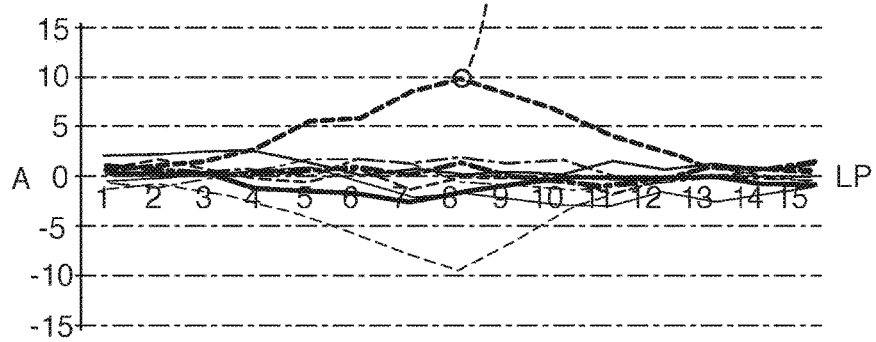
FIGS. 9A-9B show the same matrix as in FIG. 8A in FIG. 9A after forming a moving average over five probe widths in each case and the corresponding smoothed signal amplitudes in FIG. 9B.

FIG. 9A shows the same matrix as in FIG. 8A, but after forming a moving average over five probe widths in each case. FIG. 9B shows the corresponding smoothed signal amplitudes.

Forming the average is carried out in such a way that a moving average is formed over a configurable number of probe tracks within a basis matrix. In the shown example of a rotating system, the average is formed in the longitudinal direction of the pipe, i.e. parallel to the pipe axis. In a stationary system, the smoothing direction or evaluation direction would be identical to the transverse direction of the pipe. To the extent that the noise occurs stochastically in the individual probe tracks, for example due to uniformly distributed surface roughness of the test object, the signal-to-noise (S/N) ratio improves as a result of this averaging over e.g. five probes. This is immediately identifiable by comparing FIGS. 8B and 9B.

As an alternative or in addition to forming a moving mean, in which the sum of the signal amplitudes of the captured individual probes is divided by the number of captured individual probes, forming a sum would also be possible; in this case, the division by the number of detected probes would be dispensed with. Other evaluations with a low-pass characteristic, for example low-pass filtering, are also suitable, as a matter of principle, to achieve smoothing of the probe signals and hence a reduction in the dynamics. In general, it is also possible to apply different types of filtering, convolutions or correlations over a plurality of probe tracks.

The number of testing tracks underlying the averaging or filtering is configurable in some embodiments. If necessary, the number may be selected differently for each evaluation channel. In the exemplary case, it is guided by the minimum fault length of the respective evaluation channel for a specific fault type. Here, the minimum fault length is the fault length from which the maximum amplitude, i.e. the highest testing sensitivity, is reached. In contrast to conventional testing systems, in which the probe width is fixedly predetermined by the minimum fault length, the minimum fault length is now configurable in the proposed system for each type of fault. Inter alia, this results in the advantage that this improves the reproducibility of faults which are shorter than the minimum fault length. This improvement emerges independently of the length of the faults and independently of a possible overlap of the probes.

The evaluation is not restricted to evaluating directions extending parallel or perpendicular to the axis of the test object. Rather, it is also possible within a basis matrix to form moving averages or summed values or other values, which are establishable by combined evaluations of spatially dependent signal data, at any angle position transversely to the longitudinal direction and circumferential direction. In the shown exemplary embodiment, the number of evaluation channels and the angle position thereof are configurable. Alternatively, or additionally, it is also possible to predetermine whole angle regions and angle increments within angle regions in the testing apparatus. The evaluation software then ascertains the moving averages or summed values or other values for all configurable angle positions or for each individual step within a predetermined angle range.

The evaluation channels serve to capture oblique faults at any angle position. In a testing apparatus which combines a rotating system with a stationary system, angle positions from −45° (so-called "left-hand faults") to +45° (so-called "right-hand faults") of the pipe longitudinal axis may preferably be set or ascertained with the rotating system. Then, the stationary system may e.g. ascertain angle positions with −45° to +45° deviation from an ideal transverse fault (fault in the circumferential direction). Hence, faults in all orientations may reliably be found in the case of combined testing with rotating systems and stationary systems.

By way of example, automatic ascertaining of the angle position of a fault may be carried out by virtue of the signal maxima within the angle range being ascertained after ascertaining the moving averages (or summed values) for the individual angle steps. What is additionally taken into account in the exemplary embodiment is that a characteristic and calculable signal drop emerges as a result of an increasing oblique position of a fault relative to the profile of the field lines of the magnetization field. This is because it is well known that the height of a leakage flux signal reduces the further the fault or the orientation of the fault deviates from the ideal orthogonal position in relation to the main magnetization direction. This signal drop may be compensated by virtue of the signals being amplified dependent upon the configured or found angle position. Alternatively, or additionally, it is also possible for the thresholds at which a signal amplitude is considered to be indicative for a defect to be set lower than in the case of pure longitudinal faults or transverse faults. This oblique fault compensation is taken into account when forming the average for oblique faults, for example by virtue of this being carried out before or after the actual formation of the average such that, during the average formation, comparable signal amplitude values are combined with one another by calculation.

Figures 10A, 10B:
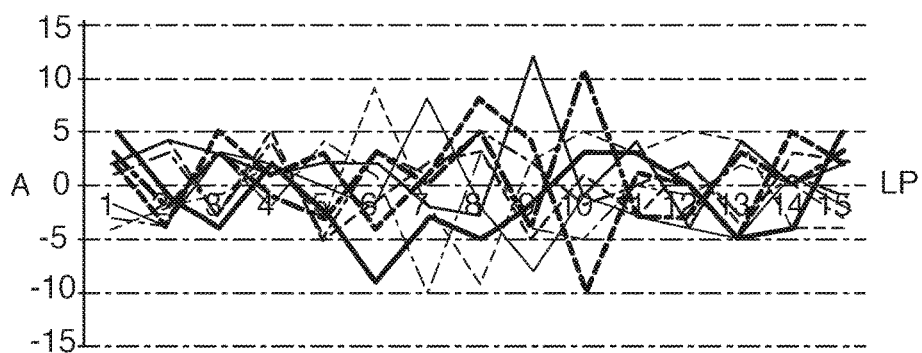
FIGS. 10A-10B show illustrations corresponding to the illustrations from FIGS. 8A-8B for an oblique fault detection with forming an average in an oblique direction.
Figures 11A, 11B, 12:
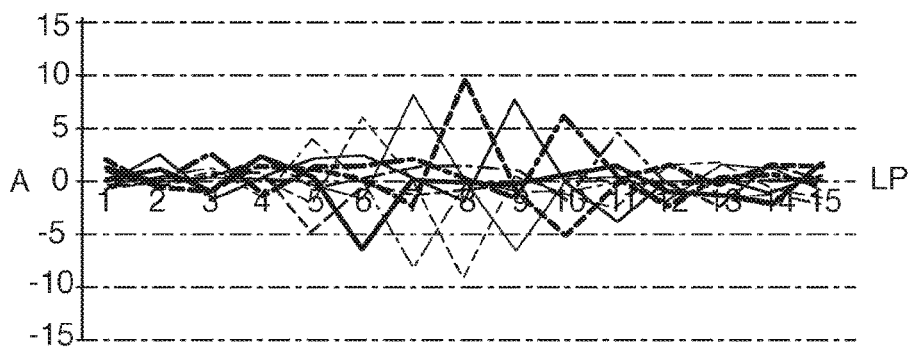
FIGS. 11A-11B show illustrations corresponding to the illustrations from FIGS. 9A-9B for an oblique fault detection after forming the average in the oblique direction.
FIG. 12 shows an evaluation of oblique faults in different evaluation directions.

For explanatory purposes, FIG. 10A shows an illustration corresponding to FIGS. 8A and 9A of an oblique fault (shaded in gray) which lies at −45° in relation to the longitudinal direction and transverse direction ("left-hand fault"). FIG. 10B shows the corresponding signal amplitudes A prior to forming the average. FIG. 11A shows the same basis matrix, but after forming the moving average over 5 probe widths in the −45° direction in each case. FIG. 11B shows the corresponding smoothed signal amplitudes.

FIG. 12 is used to show, in an exemplary manner, that forming an average (or a different type of evaluation) for oblique faults may be carried out in a plurality of different oblique directions, i.e. also in those directions which deviate by more or less than 45° from a longitudinal direction or circumferential direction. In general, this therefore allows an angle-dependent evaluation of the signal amplitudes to be carried out by way of the spatially dependent signal data of the basis matrix.

Elongate, metallic material to be tested may have disturbance zones caused by production and/or caused by processes, said disturbance zones usually extending in the longitudinal direction of the material to be tested or under small angles obliquely to the longitudinal direction. By way of example, the disturbance zones may be the longitudinally extending welding seam in the case of welded pipes. Systematic wall thickness deviations, so-called inner polygons, may occur in pipes which run through a stretch-reducing mill. Such systematic material inhomogeneities may lead to disturbance signals which impair the defect testing. The signals from these direction-oriented disturbance zones may be suppressed by means of a so-called difference operation in one embodiment. To this end, a difference-forming unit DIFF is provided in the apparatus from FIG. 6, said difference forming unit undertaking interference elimination after the fault—type-dependent filtering and forming the matrices, but before forming the moving averages or summed values.

Figure 13A:
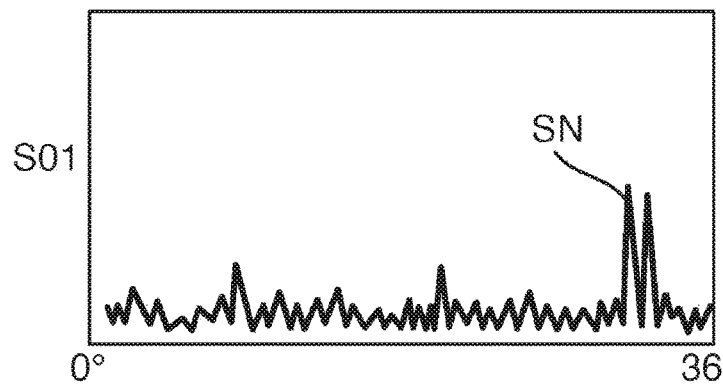
FIGS. 13A-13C show signal curves in the case of a difference-forming operation, with FIG. 13A and FIG. 13B showing signals of two probes of a rotating system lying at a difference distance from one another and FIG. 13C showing the difference signal.
Figure 13B:
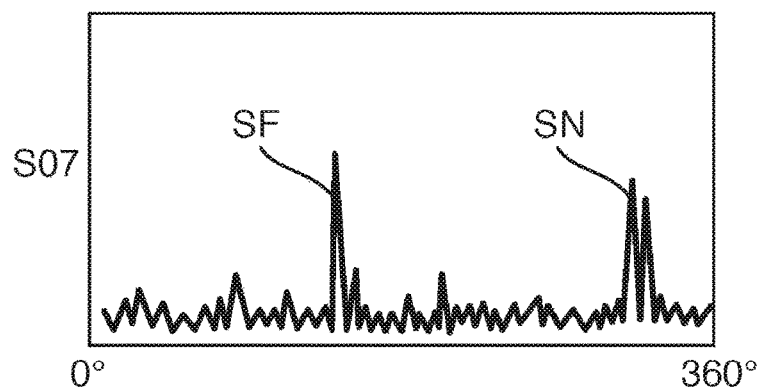
Figure 13C:
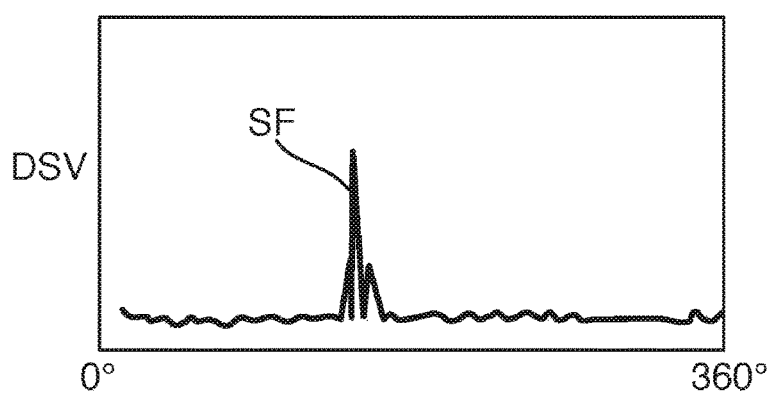

For the purposes of explaining the principle, FIG. 13 shows, in 13A, the probe signal from a first probe SO1, including the signal SN of a welding seam, in the case of a rotation between 0° and 360°. FIG. 13B shows the signal from the seventh probe SO7 of a probe array over the same angle range, wherein the signal SN of the welding seam occurs at the same angle position but, in addition, the signal SF of a fault may be identified at approximately 100°. FIG. 13C shows a difference signal curve DSV, in which the signal of the first probe SO1 was subtracted from the signal of the seventh probe SO7 in a difference-forming operation. It is possible to identify that the same signal of the welding seam occurring in both signals disappears when the difference is formed and also that the noise amplitude is reduced, while the signal SF of the fault is maintained. Hence, very efficient disturbance suppression is possible by forming a difference.

When using probe arrays with a small probe width, i.e. in the case of high resolution leakage flux testing, it is now possible to set the difference basis, i.e. the difference distance between the probes used for forming the difference, to the optimum difference distance for the respective fault type in small increments with a resolution of one probe track width. To this end, the difference-forming unit contains an adjusting device for adjusting the difference distance. An optimum difference basis is found when the difference distance is selected to be as small as possible so that small deviations in the longitudinal alignment of the sources of disturbance do not impair the suppression of the disturbance signals too strongly. On the other hand, the difference basis should be greater than the typical fault length of the respective evaluation channel because otherwise forming the difference may reduce the maximum possible averages or summed values of the fault lengths which are typical for the respective evaluation channel. Here, the typical fault length is the sum of the probe track widths when calculating the moving averages.

In the apparatus from FIG. 6, the various evaluating operations are followed by the fault detection, which is carried out by means of a fault detection unit DET, e.g. by comparing the incoming signals with predeterminable thresholds (threshold comparison). In a subsequent decision unit ENT, a decision is made according to predetermined criteria as to whether a relevant defect is present, which defect may then, for example, be marked by means of a color on the test object in a subsequent marking unit.

Furthermore, it is possible to configure, or automatically ascertain, in addition, arbitrary further angle positions for the difference operation in the exemplary embodiment of the testing apparatus such that it is possible to suppress not only the disturbance zones extending in the longitudinal direction, but also signals of sources of disturbance which extend obliquely, in the respective evaluation channels.

In the described evaluation of the difference formation, the signs of the leakage flux signals are observed and maintained in the present case. As a result, phase information arises, from which the position of the fault on the test material may be reconstructed. It is also possible to form a plurality of difference values. In one example, a signal train is ascertained in the transportation direction of the material to be tested and a signal train is ascertained counter to this transportation direction. Subsequently, the mean value of the two differences is formed. This results in a signal maximum at the original spatial position of the fault and two signals to the left and right thereof with in each case half the signal amplitude. Hence, a more accurate position determination of the fault is also possible during difference operation.

Numerous further variants are possible. By way of example, it is possible to use not a rectified leakage signal but a peak-to-peak value within a search path for evaluating the fault depth. This results in an improvement in the reproducibility of, predominantly, faults with frequencies in the vicinity of the band-pass limits.

The options described here for evaluating probe signals with the aid of a basis matrix may also be used in conjunction with other probe types for non-destructive electromagnetic material testing. By way of example, signals from eddy current probes or ultrasonic probes may be processed further in an analogous manner. In accordance with a more general phrasing, the following is therefore also disclosed:

A method for electromagnetic testing of material to be tested for detecting defects, in which a surface of the material to be tested is scanned by means of a probe arrangement for capturing electromagnetic fields caused by defects, said probe arrangement comprising a probe array with a multiplicity of probes arranged next to one another in a first direction and held at a finite testing distance from the surface of the material to be tested during the testing, and electrical probe signals are evaluated by means of an evaluating device for qualifying the defects, characterized in that an evaluation of the probe signals comprises the following steps: a mapping operation, in which signal information representing the probe signal is linked to spatial information representing the creation location of a probe signal for each probe signal in order to form spatially dependent signal data, a matrix-forming operation, in which the spatially dependent signal data (or signal data derived therefrom) are stored in fields, assigned with the correct location, of a basis matrix, and at least one evaluating operation, in which spatially dependent signal data from at least two fields of the basis matrix, (directly or indirectly) adjacent to one another in an evaluating direction, are linked to one another using at least one evaluating algorithm.

The invention claimed is:

1. A method for leakage flux testing of ferromagnetic material to be tested, for detecting defects, the method comprising the steps of:
   magnetizing a test volume of the material to be tested by a constant magnetic field;
   scanning a surface of the material to be tested by a probe arrangement for capturing magnetic leakage fields caused by defects, said probe arrangement comprising a probe array with a multiplicity of magnetic-field-sensitive probes arranged next to one another in a first direction and held at a finite testing distance from the surface of the material to be tested during the testing, wherein the probes of the probe arrangement each have a probe width in the first direction which lies in the range from 20% of the testing distance up to 10 mm; and
   evaluating electrical probe signals for qualifying the defects, wherein
   the step of evaluating the electrical probe signals comprises the following steps:
      a mapping operation, in which signal information representing the probe signal is linked to spatial information representing the creation location of a probe signal for each probe signal in order to form spatially dependent signal data,
      a matrix-forming operation, in which the spatially dependent signal data, or signal data derived therefrom, are stored in fields, assigned with the correct location, of a basis matrix, and
      at least one evaluating operation, in which spatially dependent signal data from at least two fields of the basis matrix, adjacent to one another in an evaluating direction, are linked to one another using at least one evaluating algorithm.

2. The method as claimed in claim 1, wherein bipolar signal information is used when forming the basis matrix.

3. The method as claimed in claim 1, further comprising the step of:
   pre-filtering of the probe signals, carried out before the mapping operation, by a band-pass filter with adjustable limit frequencies, wherein a lower limit frequency is set to a lowest frequency of the probe signals to be expected and an upper limit frequency is set to a highest frequency of the probe signals to be expected.

4. The method as claimed in claim 3, further comprising the step of:
   filtering, by one or more band-pass filters with adjustable limit frequencies, carried out after the mapping operation, said filtering depending on a fault type, wherein a lower limit frequency of a band-pass filter is set to a lowest frequency of the probe signals and an upper limit frequency of the band-pass filter is set to a highest frequency of the probe signals, respectively to be expected for a predetermined fault type.

5. The method as claimed in claim 4, wherein a number of band-passes for the filtering depending on the fault type is configurable and, two, three, four or more band-pass filters with different limit frequencies are used for the filtering depending on the fault type.

6. The method as claimed in claim 1, wherein one or more evaluating operations are carried out, which are designed as filtering operations of spatially dependent signal data over a predetermined number of mutually adjacent fields in a predetermined evaluating direction.

7. The method as claimed in claim 1, wherein an evaluating operation comprises a smoothing operation of spatially dependent signal information data over a predeterminable number of mutually adjacent fields in a smoothing direction, wherein the smoothing operation comprises forming a moving average or low-pass filtering.

8. The method as claimed in claim 7, wherein the evaluating direction of the smoothing operation corresponds to the first direction, wherein a number of probes taken into account during the smoothing operation is selected such that an effective probe width which is adapted to a minimum fault length is generated.

9. The method as claimed in claim 1, wherein the evaluating direction corresponds to a second direction extending perpendicular to the first direction, wherein fault-type-dependent band-pass filtering is carried out in the second direction.

10. The method as claimed in claim 9, wherein the evaluating direction corresponds to an oblique direction which extends transversely in relation to the first direction and transversely in relation to the second direction.

11. The method as claimed in claim 10, further comprising:
an oblique fault compensating operation, in which an angle difference between an oblique fault direction and a field line direction of the magnetization field is determined and signal data of an oblique fault are corrected by a compensation factor dependent on the angle position.

12. The method as claimed in claim 11, further comprising:
automatically ascertaining the angle position of oblique faults extending in the oblique direction which extends transversely in relation to the first direction and transversely in relation to the second direction, wherein the automatic ascertaining is carried out over a plurality of oblique directions in different evaluating directions within a predeterminable angle range automatically, the oblique direction with a maximum mean signal amplitude being ascertained taking into account the angular dependence of the signal amplitude.

13. The method as claimed in claim 1, further comprising:
a difference-forming operation, in which a difference between spatially dependent signal information data of two fields lying in a difference-forming direction and at a difference distance from one another is ascertained.

14. The method as claimed in claim 13, wherein
the difference-forming direction corresponds to the first direction,
the difference-forming direction extends obliquely to the first direction, and/or
a plurality of difference-forming operations are carried out in different difference-forming directions and/or over different difference distances.

15. The method as claimed in claim 14, wherein the difference distance is matched to the minimum fault length, wherein the difference distance lies between the minimum fault length and five times the minimum fault length.

16. The method as claimed in claim 1, wherein the ferromagnetic material to be tested is a ferromagnetic pipe.

17. An apparatus for leakage flux testing of ferromagnetic material to be tested for detecting defects, comprising:
a magnetization device for magnetizing a test volume of the material to be tested;
a probe arrangement for scanning a surface of the material to be tested for capturing magnetic leakage fields caused by defects, wherein the probe arrangement comprises a probe array with a multiplicity of magnetic-field-sensitive probes arranged next to one another in a first direction and held at a finite testing distance from the surface of the material to be tested during the testing, and
an evaluating device for evaluating signals from the probes for qualifying the defects, wherein
the probes of the probe array each have a probe width in the first direction which lies in the range from 0% of the testing distance up to 10 mm,
the evaluating device is configured to perform:
a mapping operation, in which signal information representing the probe signal is linked to spatial information representing the creation location of a probe signal for each probe signal in order to form spatially dependent signal data,
a matrix-forming operation, in which the spatially dependent signal data, or signal data derived therefrom, are stored in fields, assigned with the correct location, of a basis matrix, and
at least one evaluating operation, in which spatially dependent signal data from at least two fields of the basis matrix, adjacent to one another in an evaluating direction, are linked to one another using at least one evaluating algorithm.

18. The apparatus as claimed in claim 17, wherein the apparatus is configured to test ferromagnetic pipes.

* * * * *